United States Patent [19]

Gersdorff

[11] Patent Number: 4,740,209
[45] Date of Patent: Apr. 26, 1988

[54] STABILIZER FOR A MIDDLE-EAR COLUMELLATE PROSTHESIS

[76] Inventor: Michel Gersdorff, 24, Avenue des Myrtilles, B-1950 Kraainem, Belgium

[21] Appl. No.: 3,082

[22] Filed: Jan. 14, 1987

[30] Foreign Application Priority Data

Jan. 27, 1986 [FR] France ............................... 86 01074

[51] Int. Cl.$^4$ ............................ A61F 2/18; A61F 2/28
[52] U.S. Cl. .......................................... 623/10; 623/16
[58] Field of Search ............................... 623/10, 16, 18

[56] References Cited

U.S. PATENT DOCUMENTS

| | | | |
|---|---|---|---|
| 3,196,462 | 7/1965 | Robinson | 623/10 |
| 3,931,648 | 1/1976 | Shea | 623/10 |
| 4,281,419 | 8/1981 | Treace | 623/10 |
| 4,601,723 | 2/1986 | McGrew | 623/10 |

FOREIGN PATENT DOCUMENTS 1041110A  9/1983  U.S.S.R. ............................... 623/10

OTHER PUBLICATIONS

Search Report FR8601074 including 1 annex page.

Primary Examiner—Ronald L. Frinks
Attorney, Agent, or Firm—Ladas & Parry

[57] ABSTRACT

A stabilizer (18) for a total or partial middle-ear prosthesis ending in a columella (23) bearing against the base (8) of the stapes. The stabilizer (18) has a plane substantially oval support surface (19) which matches the shape of the surface of the base (8) and is received between the remnants (20) of the stapedial arch (7). The body of the stabilizer (18) narrows from its support surface (19) to a substantially cylindrical end portion (21) and is provided at its center with a cylindrical through hole (22) which matches and receives the cylindrical contour of the end of the columella (23). This stabilizer (18) prevents the lateral displacement of the columella (23) on the base (8) and maintains sound transmission between the latter and the columella.

2 Claims, 2 Drawing Sheets

STABILIZER FOR A MIDDLE-EAR COLUMELLATE PROSTHESIS

BACKGROUND OF THE INVENTION

1. Field of the invention.

The present invention relates to a stabilizer for a total or partial middle-ear prosthesis ending in a columella bearing against the base of the stapes.

The natural mechanism for the transmission of sonic vibrations from the tympanum to the inner ear functions via the ossicular chain. The fenestra of the vestibule, in which the stapes (the smallest of the ossicles) lies, provides communication between the middle ear and the inner ear. The transmission mechanism functions through three articulated ossicles; the malleus, the incus, and the stapes, which amplify the vibrations of the tympanum for transmission of sound to the inner ear.

Numerous pathologies of the middle ear (chronic otitis media in different forms, injuries, sequelae of previous operations) may result in dysfunction of the tympano-ossicular complex. This dysfunction entails a hearing impairment in the form of conduction deafness, that is to say impairment of the auditory function characterized by failure to achieve correct transmission of the sound message propagated from the external ear to the inner ear.

If the middle ear, which functions essentially as an acoustic impedance transformer, cannot perform this function, the cochlear input signal is diminished and so-called conduction deafness results.

Such conduction deafness is principally associated with damage to the tympanum (perforation of the tympanum), or with injury to the ossicular chain (ankylosis or ossicular lysis).

The present invention relates more particularly to a stabilizer for prostheses intended for the reconstruction of the ossicular chain for the purpose of safeguarding transmission of sound.

The reconstruction of the different bony parts of the middle ear or external ear is possible by means of ossicular alloplasty (ossicle taken from a donor) or by means of ossicular autoplasty (removal of one of the patient's ossicles, remodelling and restoration of tympano-ossicular continuity), or, more recently, by fitting a prosthesis made of a so-called biocompatible material. In recent years use has in particular been made of porous polyethylenes (such as the porous polyethylene marketed under the trade mark Proplast®) or of biocompatible ceramics, particularly bioactive biocompatible ceramics (such as that marketed under the trade mark Ceravital®), the slow superficial dissolution of which permits reossification and excellent contact between the tympanum or the neotympanum and the ceramic prosthesis.

2. Description of the prior art.

The reconstruction of the sound transmission mechanism in the middle ear by the implantation of biocompatible prostheses is well known.

Various forms of ossicular prostheses exist. A distinction is in particular made between so-called total prostheses and so-called partial prostheses. A total prosthesis is fitted directly between the tympanum (or the neotympanum) and the base of the stapes. A partial prosthesis is intended to replace only a part of the ossicular chain (the remainder of the ossicular chain being intact). The principal known partial prostheses are those intended to be fitted between the tympanum (or the neotympanum) and the head of the stapes, and also those partial prostheses which are intended to be fitted between the end of the process of the incus and the base of the stapes.

Most total prostheses used at the present time are prostheses functioning in the form of columellae, that is to say the entire ossicular chain (malleus, incus, stapes) is replaced by a single prosthesis interposed directly between the tympanum or the neotympanum and the base of the stapes (see for example U.S. Pat. No. 4,510,627 and FIG. 2).

The Applicant's co-pending patent application of the same date describes an articulated total prosthesis ending in a columella bearing against the base of the stapes. This columella replaces the stapedial arch.

It often happens that of the ossicles of the middle ear the malleus and the incus are still intact, while the stapedial arch of the stapes is damaged. The arch is then also replaced by a small columella (see U.S. Pat. No. 3,196,462 and FIG. 3, and also U.S. Pat. No. 3,391,648 and FIG. 4).

Depending on the type of prosthesis, the columella of biocompatible material may be of porous material, such as polyethylene, of polytetrafluoroethylene, or of ceramic or bioactive ceramic material (for example Ceravital®).

In all cases where the middle-ear prosthesis ends in a columella bearing against the base of the stapes it is impossible to fasten the end of the columella in a mechanically secure manner on the base. There is consequently a risk of lateral displacement of the columella and a risk of loss of contact with the base as the result of contraction of the neotympanum during the process of postoperative cicatrization, or for any other reason, with loss of sound transmission.

SUMMARY OF THE INVENTION

The present invention therefore relates to a stabilizer for a total or partial middle-ear prosthesis ending in a columella bearing against the base of the stapes. The stabilizer according to the invention has a plane support surface which matches the shape of the surface of the base of the stapes between the two remnants of the stapedial arch, this support surface being intended to be received between these remnants. The body of the stabilizer narrows from its support surface to a substantially cylindrical end portion situated vertically in line with the middle of the support surface and provided with a central cylindrical through hole matching the cylindrical contour of the end of said columella bearing against the base, this cylindrical aperture being intended to receive the end of said columella.

One example of construction of the stabilizer according to the invention is described below with reference to the accompanying drawings, in which like reference numerals designate like elements.

DETAILED DESCRIPTION OF THE INVENTION

Figure 1:
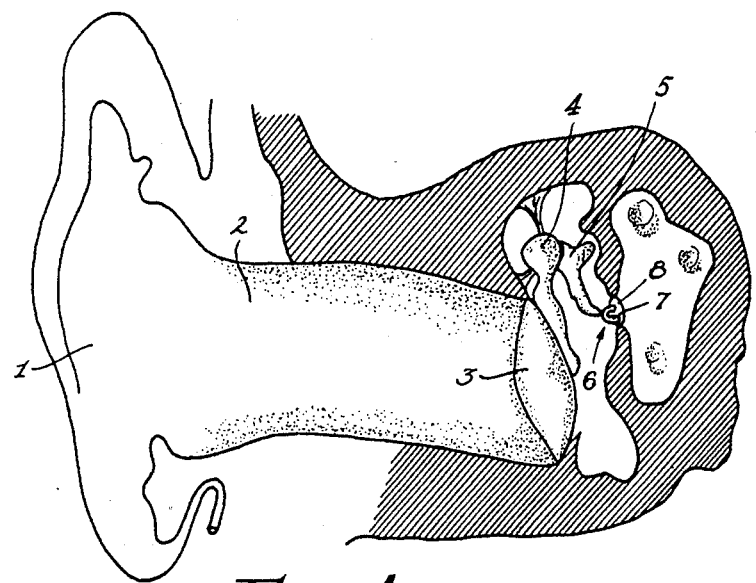
FIG. 1 is a schematic elevation, partly in section, of the extended ear and the middle ear.

FIG. 1 shows the auricle of the external ear 1, the external auditory meatus 2, the tympanic membrane 3, and the middle ear consisting of its three articulated ossicles: the malleus 4, the incus 5 and the stapes 6 with its stapedial arch 7, and the base 8 of the stapes.

Figure 2:
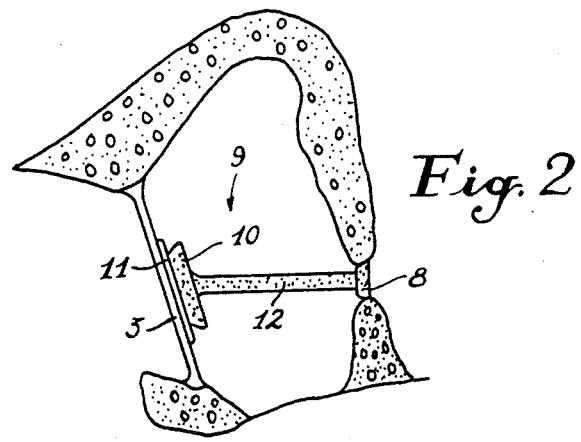
FIG. 2 is a schematic elevation of the middle ear, in which the ossicles are replaced by a columellate prosthesis according to U.S. Pat. No. 4,510,627.

FIG. 2 shows a total middle-ear prosthesis 9 consisting on the one hand of a widened round head 10 adhering to the tympanic membrane 3 by means of a cartilage 11, and on the other hand of an elongate rod (columella) 12 bearing against the base 8 of the stapes.

Figure 3:
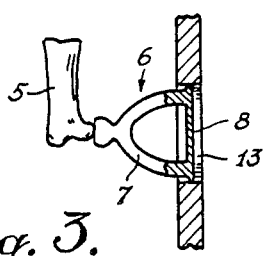
FIG. 3 is a schematic elevation on a larger scale of the joint between the incus and the stapes.

FIG. 3 shows the articulation between the end of the incus 5 and the stapes 6 with its stapedial arch 7 and the base 8 of the stapes in the oval window 13.

Figure 4:
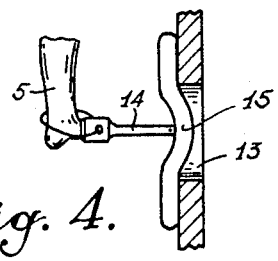
FIG. 4 is a schematic elevation of a columellate prosthesis replacing the stapedial arch according to U.S. Pat. No. 3,196,462.

FIG. 4 shows a prosthesis in the form of a columella 14, on the one hand fixed to the end of the incus 5 and on the other hand leading to the oval window 13 and bearing either against the base of the stapes when the latter is retained (not illustrated) or against a membrane 15 interposed over the oval window (a vein or perichrondrium).

Figure 5:
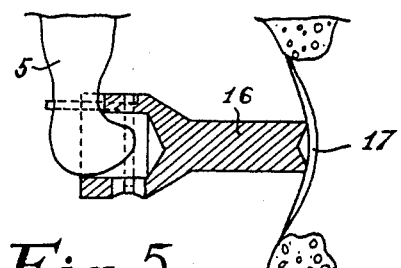
FIG. 5 is a schematic elevation of another columellate prosthesis replacing the stapedial arch according to U.S. Pat. No. 3,931,648.

FIG. 5 shows another prosthesis, likewise in the form of a columella 16, fixed in a different manner on the incus 5 and likewise leading into the oval window, over which a membrane 17 is placed.

Figure 6:
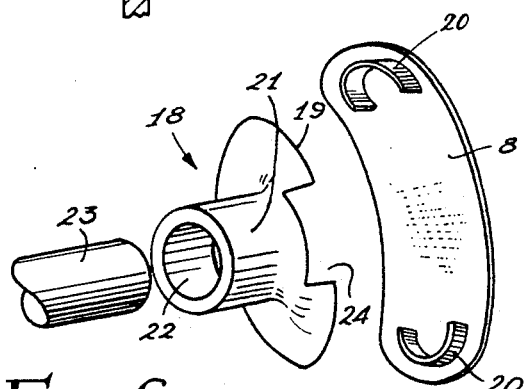
FIG. 6 is an exploded view of the stabilizer according to the invention, between the base of the stapes and the end of columella.
Figure 7:
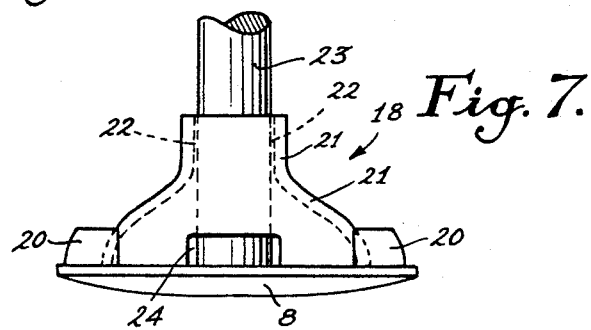
FIG. 7 is a view in section of the stabilizer according to the invention in position on the base of the stapes between the remnants of the stapedial arch, with the end of a columella passing through it.

FIGS. 6 and 7 show a stabilizer 18 according to the present invention, whose support surface 19 matches the shape of the surface of the base 8 of the stapes between the two remnants 20 of the stapedial arch 7. The stabilizer 18 is intended to fit with its support surface 19 between these remnants 20. The stabilizer 18 has a substantially cylindrical end portion 21 provided with a central cylindrical through hole 22 through which passes the longitudinal axis of the stabilizer, the through hole 22 matching the cylindrical contour of the bottom end of a columella 23 forming part of the middle-ear prosthesis. The cylindrical hole 22 is intended to receive the end of the columella 23 for bearing against the base 8 of the stapes. The cylindrical end portion 21 gradually widens to a substantially oval support surface 19 limited by a plane perpendicular to the longitudinal axis passing through the central hole 22 for matching the shape of the surface of base 8 of the stapes and is adapted to be received between the remnants 20 of the stapedial arch 7.

In a preferred form the bottom part of the cylinder of the stabilizer 18 may have two side apertures 24 at right angles to the axis between the remnants 20 of the stapedial arch 7, which permit the passage of air from the cylindrical hole 22 to the outside, but which also permit observation of the bottom end of the columella 23 while it is being placed in position, and even enable the stabilizer 18 to be bonded to the base 8 of the stapes by means of physiological adhesive. This also enables the columella 23 to move unhampered in the cylindrical aperture 22 in the stabilizer, without sacrificing the transmission of sound from the columella 23 to the base 8 via the cylindrical aperture 22 of the stabilizer 18, through a frictional or piston action, every time the columella 23 loses direct contact with the base 8 of the stapes, for example as the result of contraction of the neotympanum during postoperational cicatrization.

The stabilizer 18 also has the advantage of holding the columella 23 in the center of the base 8 of the stapes, and of avoiding any lateral displacement, such as was hitherto a shortcoming of practically all middle-ear prosthesis ending in a columella.

I claim:

1. A stabilizer (18) for a total or partial middle-ear prosthesis ending in a cylindrical columella (23) adapted for bearing against the base (8) of the stapes, said stabilizer (18) comprising a substantially cylindrical end portion (21) provided with a central cylindrical through hole (22) through which passes a longitudinal axis of the stabilizer, said cylindrical through hole (22) matching the cylindrical contour of the end of said columella (23) for bearing against the base (8) and being intended to receive the end of said columella (23), said cylindrical end portion (21) gradually widens to a substantially oval support surface (19) limited by a plane perpendicular to the longitudinal axis passing through the central hole (22), said support surface (19) adapted for matching the shape of the surface of the base (8) of the stapes between two remnants (20) of the stapedial arch (7) and said support surface (19) being adapted to be received between said remnants (20).

2. A stabilizer (18) as claimed in claim 1, wherein said stabilizer (18) is provided at the long sides of its support surface (19) with two side apertures (24) at right angles to said longitudinal axis, which apertures (24) permit the passage of air from the interior of the cylindrical hole (22) to the outside.

* * * * *